United States Patent [19]

Nag

[11] Patent Number: 5,824,315
[45] Date of Patent: Oct. 20, 1998

[54] BINDING AFFINITY OF ANTIGENIC PEPTIDES FOR MHC MOLECULES

[75] Inventor: Bishwajit Nag, Fremont, Calif.

[73] Assignee: Anergen, Inc., Redwood City, Calif.

[21] Appl. No.: 640,344

[22] Filed: Apr. 30, 1996

Related U.S. Application Data

[63] Continuation-in-part of Ser. No. 227,371, Apr. 14, 1994, and Ser. No. 329,010, Oct. 25, 1994, which is a continuation-in-part of Ser. No. 143,575, Oct. 25, 1993, abandoned.

[51] Int. Cl.$^6$ .................................................. A61K 39/00
[52] U.S. Cl. ............................ 424/195.11; 424/185.1; 424/193.1
[58] Field of Search ........................... 424/193.1, 195.11, 424/185.1

[56] References Cited

U.S. PATENT DOCUMENTS

| | | |
|---|---|---|
| 5,130,297 | 7/1992 | Sharma et al. . |
| 5,194,425 | 3/1993 | Sharma et al. . |
| 5,260,422 | 11/1993 | Clark et al. . |
| 5,399,347 | 3/1995 | Trentham et al. . |
| 5,468,481 | 11/1995 | Sharma et al. . |
| 5,595,881 | 1/1997 | Kendricks . |

FOREIGN PATENT DOCUMENTS

| | | |
|---|---|---|
| WO 91/18012 | 11/1992 | WIPO . |
| WO 94/03205 | 2/1994 | WIPO . |

OTHER PUBLICATIONS

Burnham Am. S. Hosp. Pharm 51:210, 1994.
Nihara et al Eur. J. Immunol. 26: 1736, 1996.
Lamb et al. Immunology 85: 447, 1995.
Martin et al. J. of Immunol. 148: 1359, 1992.
Karin et al. J. Exp. Med. 180:2227, 1994.
Nas et al J. of Immunol. 148: 369, 1992.
Arimilli et al. Immunol. and Cell Biology 74:99, 1996.
Nas et al J. of Biol. Chem. 271: 10413, 1996.
Nas et al. PNAS 90: 1604, 1993.
Clank et al J. of Biol. Chem. 269: 94, 1994.
Sharma et al PNAS 88: 11465, 1991.
Acha–Orbea, et al., "T Cell Receptors in Murine Autoimmune Diseases", *Ann. Rev. Immunol*, 7:371–405 (1989).
Engelhard, V.H., "How Cells Process Antigens", *Scientific American*, pp. 54–61 Aug. 1994.
Hammer, et al., "Peptide Binding Specificity of HLA–DR4 Molecules: Correlation with Rheumatoid Arthritis Association", *J. Exp. Med.* 181:1847–1855 (1994).

Hohfield, et al., "Human T–helper lymphocytes in myasthenia gravis recognize the nicotinic receptor α subunit", *Proc. Natl. Acad. Sci. USA* 84:5379–5383 (1987).
Holoshitz, et al., "T Lymphocytes of Rheumatoid Arthritis Patients show Augmented reactivity to a fraction of mycobacteria cross–reactive with cartilage", *The Lancet* ii:305–309 (1986).
Lindstrom, et al., "Myasthenia Gravis", *Adv. Immunol*, 42:233–284 (1988).
Maron, et al., "H–2K Mutation controls Immune Response Phenotype of Autoimmune Thyroiditis", *J. Exp. Med.* 152:1115–1120 (1980).
O'Sullivan, et al., "Characterization of the Specificity of Peptide Binding to Four DR Haplotypes", *The Journal of Immunology*, 145(6):1799–1808 (1990).
Rötzschke, et al., "Naturally–Occuring Peptide Antigens Derived from the MHC Class–I–Restricted Processing Pathway", *Immunology Today*, 12(12):447–455 (1991).
Stuart, et al., "Collagen Autoimmune Arthritis", *Ann. Rev. Immunol*, 2:199–218 (1984).
Tzartos, et al., "Monoclonal antibodies used to probe acetylcholine receptor structure: Localization of the main immunogenic region and detection of similarities between subunits", *Proc. Natl. Acad. Sci. USA*, 77:755–759 (1980).
van Eden, et al., "Cloning of the mycobacterial epitope recognized by T lymphocytes in adjuvant arthritis", *Nature*, 331:171–173, (1988).
Wucherpfennig, et al., "Structural Requirements for Binding of an Immunodominant Myelin Basic Protein Peptide to DR2 Isotypes and for Its Recognition by Human T Cell Clones", *J. Exp. Med.*, 179:279–290 (1994).
Wucherpfennig, et al., "Structural Basis for Major Histocompatibility Complex (MHC) —linked Susceptibility to Autoimmunity: Charged Residues of a Single MHC Binding Pocket Confer Selective Presentation of Self–Peptides in Pemphigus Vulgaris", *Proc. Natl. Acad. Sci. USA*, 92:11935–11939 (1995).

*Primary Examiner*—Thomas M. Cunningham
*Assistant Examiner*—Martha Lubet
*Attorney, Agent, or Firm*—Townsend and Townsend and Crew, LLP

[57] ABSTRACT

This invention provides methods of improving the binding affinity of a peptide epitope for MHC Class II molecules by attaching to the N-terminus of the peptide epitope a hydrophobic amino acid or a peptide containing a hydrophobic amino acid. The invention also provides complexes between the modified antigenic peptides and MHC Class II molecules, as well as method for treating deleterious immune responses.

32 Claims, 7 Drawing Sheets

```
1                                                40
GDTRPRFLEQ  VKHECHFFNG  TERVRFLDRYF  YHQEEYVRFD 41                                               80
SDVGEYRAVT  ELGRPDAEYW  NSQKDLLEQK   RAAVDTYCRH 81                                              120
NYGVGESFTV  QRRVYPEVT   VAPSKTQPLQ   HHNLLVCNVS 121                                             160
GFYPGSIEVR  WFRNGQETKA  GVVSTGLIQN   GDWTFQTLVM 161                                             200
LETVPRSGEV  YTCQVELSV   TSPLTVEWRA   RSESAQSKML

SGVG
```

FIG. 7.

BINDING AFFINITY OF ANTIGENIC PEPTIDES FOR MHC MOLECULES

This is a continuation-in-part of co-pending U.S. patent application Ser. No. 08/227,371, filed Apr. 14, 1994, pending. This application also is a continuation-in-part of co-pending U.S. patent application Ser. No. 08/329,010, filed Oct. 25, 1994, pending, which is a continuation-in-part of U.S. patent application Ser. No. 08/143,575 filed Oct. 25, 1993, now abandoned. All of the above applications are hereby incorporated by reference in their entirety.

BACKGROUND OF THE INVENTION

This invention relates to the field of cellular immunology.

In cell-mediated immunity, molecules of the major histocompatibility complex, referred to as HLA molecules in humans, present antigenic peptides to T cells. When a T cell receptor on the surface of a T cell recognizes an epitope on the antigenic peptide, the T cell can become activated. Cytotoxic T cells (CD8+) recognize cells bearing MHC class I molecules. Activated cytotoxic T cells kill infected target cells. Helper T cells (CD4+) recognize cells bearing MHC Class II molecules. Activated helper T cells promote proliferation, maturation and immunologic function of other cell types by, for example, the secretion of lymphokines.

It is believed that the presentation of antigen by the MHC glycoprotein on the surface of antigen-presenting cells (APCs) occurs subsequent to the hydrolysis of antigenic proteins into smaller peptide units. The location of these smaller segments within the antigenic protein can be determined empirically. These segments are thought to be about 8–20 residues in length, and contain both the agretope (recognized by the MHC molecule) and the epitope (recognized by T cell receptor on the T cell). The epitope is a contiguous or noncontiguous sequence of 5–6 amino acids which recognizes the antigen-specific T cell receptor. The agretope is a continuous or non-contiguous sequence which is responsible for the association of the peptide with the MHC glycoproteins.

Certain cell-mediated immune responses are deleterious to an individual. These include, for example, auto-immune diseases, allergies and allograft rejection. Antigens associated with autoimmune diseases have been identified. Many of these antigens have been found capable of binding to MHC class II molecules. For example, native type-II collagen is identified in collagen-induced arthritis in rat and mouse, and mycobacterial heat shock protein is associated with adjuvant arthritis (Stuart et al. (1984), *Ann. Rev. Immunol.* 2: 199–218; van Eden et al. (1988), *Nature* 331: 171–173.). Thyroglobulin has been identified in experimental allergic thyroiditis (EAT) in mouse (Maron et al. (1988), *J. Exp. Med.* 152: 1115–1120). The acetylcholine receptor (AChR) is associated with experimental allergic myasthenia gravis (EAMG) (Lindstrom et al. (1988), *Adv. Immunol.* 42: 233–284). Myelin basic protein (MBP) and proteolipid protein (PLP) are associated with experimental allergic encephalomyelitis (EAE) in mouse and rat (See Acha-Orbea et al., (1989) *Ann. Rev. Immunol.* 7: 377–405.)

The following target antigens are associated with autoimmune diseases in humans. In multiple sclerosis (MS), which results in the destruction of the myelin sheath in the central nervous system, myelin basic protein (MBP), the major protein component of myelin, is the principal autoantigen. Systemic lupus erythematosus (SLE) has a complex systemology, but results from an autoimmune response to several tissues including red blood cells. Peptides which are the antigenic effectors of this disease are found, for instance, in the proteins on the surface of red blood cells. Rheumatoid arthritis (RA) is a chronic inflammatory disease resulting from an immune response to proteins found in the synovial fluid. Peptide epitopes associated with rheumatoid arthritis are derived from human type II collagen. (Holoshitz et al. (1986), *Lancet ii:* 305–309). Insulin-dependent diabetes mellitus (IDDM) results from autoimmune attack on the β cells within the Islets of Langerhans. These cells are responsible for secretion of insulin. Circulating antibodies to cell surface antigens on Islet cells and to insulin are known to precede IDDM. Critical peptides in eliciting the immune response in IDDM are believed to be portions of cell surface proteins of β cells. The α subunit of the acetylcholine receptor is associated with myasthenia gravis. (See, e.g., Tzartos and Lindstrom, *Proc. Natl. Acad. Sci. USA* (1980) 77: 755, Lindstrom et al. (1988), supra, and Hohfield et al., *Proc. Natl. Acad. Sci. USA* (1987). The epitopes recognized by autoreactive T cells lie between residues 1–30, 125–147, 169–181, 257–271 and 351–368. In addition, in humans the AChR peptides 195–212 and 257–269 have been partially characterized as epitopes in myasthenia gravis patients of the HLA-DR5 and HLA-DR3, DQw2 MHC haplotypes, respectively (See Acha-Orbea (1989), supra).

MHC Class II molecules can bind exogenously supplied antigenic peptides to form MHC-peptide complexes. These complexes can inactivate T cells bearing receptors that recognize an epitope of the antigenic peptide in the antigen binding pocket of the MHC molecule. Therefore, these complexes are useful in the treatment of diseases in which the T cell is involved in a deleterious immune response, such as an autoimmune response. U.S. Pat. No. 5,468,481.

The percent of affinity-purified MHC molecules occupied with antigenic peptide varies considerably. Increasing the occupancy of MHC molecules by antigenic peptides would improve efficiency and would be an advance in the technology.

SUMMARY OF THE INVENTION

It has been discovered that the addition of a hydrophobic amino acid near the amino (N-) terminus of a peptide epitope for an MHC Class II molecule improves the binding of the peptide epitope to MHC Class II molecules and, in particular, to human HLA molecules. Accordingly, this invention provides methods of modifying peptide epitopes to have greater binding affinity for MHC Class II molecules. The invention also provides the modified antigenic peptides, themselves, complexes of MHC Class II molecules and modified peptides useful for inactivating T cells, and therapeutic methods of inactivating unwanted immune responses in a subject by administering the complexes to the subject.

More particularly, this invention provides modified antigenic peptides for MHC Class II molecules having the amino acid sequence Y-Z. Y- is a hydrophobic amino acid moiety or a peptide moiety having about 1–5 amino acids wherein at least one of the amino acids is a hydrophobic amino acid. Z- is a peptide epitope moiety for the MHC class II molecule. The modified antigenic peptide has a higher binding affinity for the MHC Class II molecule than the peptide epitope. Preferably, the hydrophobic amino acid is tyrosine, which is the N-terminal amino acid residue of the modified antigenic peptide. The modified antigenic peptide preferably binds to an HLA molecule, for example, HLA-DR2 or HLA-DR4.

This invention also provides methods of increasing the binding affinity of a peptide epitope of an MHC Class II molecule. The methods involve providing a peptide epitope for the MHC class II molecule, and attaching to the N-terminus of the peptide epitope a hydrophobic amino acid or a peptide having 1–5 amino acids wherein at least one of the amino acids is a hydrophobic amino acid.

In another aspect, this invention provides MHC Class II-modified peptide complex consisting essentially of an MHC Class II component having an antigen binding site; and a modified peptide antigen of this invention. The complexes can include an intact extracellular domain of an MHC Class II molecule or an MHC Class II single chain. In one embodiment, the complex also includes an effector component capable of killing a T cell.

In another embodiment, complex is a fusion protein. Fusion proteins can be produced by expressing recombinant nucleic acid molecules encoding a single polypeptide chain including both the MHC Class II component having an antigen binding site and the modified antigenic peptide.

In another aspect, this invention provides pharmaceutical compositions including a pharmaceutically acceptable excipient and an MHC Class II-modified peptide complex capable of binding a T cell receptor. Methods for preparing such a pharmaceutical composition involve isolating the MHC Class II component from a cell capable of producing the component; contacting the MHC Class II component with the peptide such that the peptide is linked to the antigen binding site, thereby forming an MHC Class II-peptide complex; removing excess peptide not linked to the antigen binding site; and mixing the MHC Class II-modified peptide complex with the pharmaceutically acceptable excipient in a ratio suitable for therapeutic or diagnostic administration of the complex.

The pharmaceutical compositions of the invention are useful in methods of inactivating an autoreactive T cell associated with a deleterious immune response in a subject in need thereof. The methods involve administering to the subject an effective amount of the pharmaceutical composition. This invention also provides methods of treating a subject in need of prophylactic or therapeutic treatment of a deleterious immune response involving administering to the subject an effective amount of a pharmaceutical composition of the invention. In such methods, the peptide epitope can include an epitope of myelin basic protein recognized by a T cell associated with multiple sclerosis, an epitope from type-II collagen recognized by a T cell associated with rheumatoid arthritis, an epitope of a red blood cell surface protein recognized by a T cell associated with systemic lupus erythematosus, an epitope from a cell surface antigen of a β cell of the Islets of Langerhans recognized by a T cell associated with insulin-dependent diabetes mellitus, an epitope from the α subunit of the acetylcholine receptor recognized by a T cell associated with myasthenia gravis or an epitope of myelin basic protein recognized by a T cell associated with multiple sclerosis.

The complexes of this invention also are useful for determining whether a subject has autoreactive T cells against a peptide epitope. The methods involve contacting a sample from the subject with an MHC Class II-modified peptide complex of this invention and determining whether the MHC Class II-modified peptide complex has bound to a T cell in the sample. Binding indicates that the subject has the autoreactive T cell.

BRIEF DESCRIPTION OF THE DRAWINGS

FIG. 7 shows the amino acid sequence of HLA-DR4Dw4 (SEQ ID NO:18).

DETAILED DESCRIPTION OF THE INVENTION

I. Modified Antigenic Peptides

Figure 1:
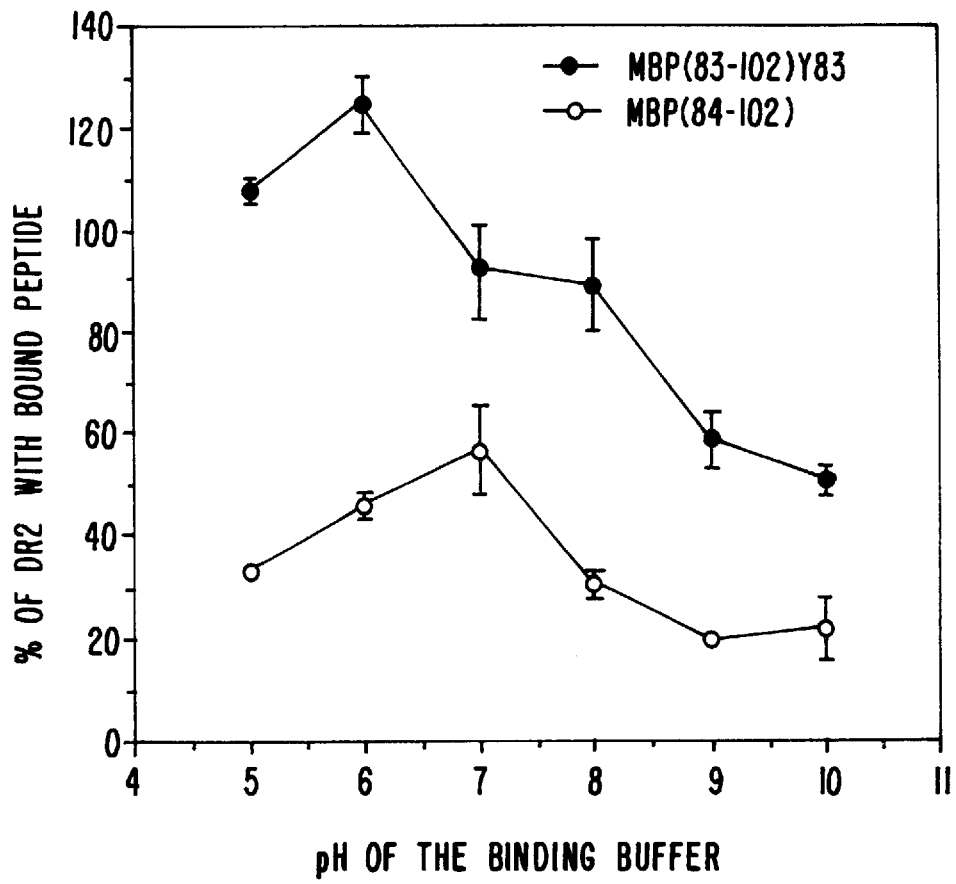
FIG. 1 compares the percent of purified DR2 bound with MBP(84–102) peptide with the percent MBP(83–102)Y83 peptide at various pH.

Modified antigenic peptides for MHC class II molecules have the amino acid sequence Y-Z. Y- is a hydrophobic amino acid moiety or a peptide moiety having about 1–5 amino acids wherein at least one of the amino acids is a hydrophobic amino acid. Z- is a peptide epitope moiety for an MHC class II molecule. The modified antigenic peptide has a higher binding affinity for the MHC Class II molecule than does the peptide epitope, alone.

As used herein, the term "peptide" refers to a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. Commonly encountered amino acids which are not gene-encoded may also be used in the present invention. All of the amino acids used in the present invention may be either the D- or L-isomer. The L-isomers are preferred. In addition, other peptidomimetics are also useful in the peptides of the present invention. For a general review see A. F. Spatola, in *Chemistry and Biochemistry of Amino Acids, Peptides and Proteins,* B. Weinstein, eds., Marcel Dekker, New York, p. 267 (1983). The term also encompasses peptides that have been modified by, for example, phosphorylation, glycosylation or lipidation.

A. The Peptide Epitope

The peptide epitope moiety is the radical of a peptide that is capable of binding to the antigen binding pocket of an MHC Class II molecule. A peptide epitope can have between about 8 and about 50 amino acids, about 8 and about 30 amino acids, about 8 and about 20 amino acids, about 8 and about 15 amino acids or 9 amino acids. Peptide epitopes also can be considerably longer. Peptide epitopes include those having sequences from fragments of naturally occurring antigens, and synthetic, non-natural sequences, each characterized by its ability to bind to an MHC Class II molecule.

Preferably, the peptide epitope comprises an epitope that is recognized by a T cell involved in a deleterious immune response and, in particular, in an auto-immune disease. Auto-antigenic antigens, i.e., antigens associated with various autoimmune diseases, are particularly useful as sources of peptide epitope moieties. The peptide epitope can comprise an epitope of myelin basic protein recognized by a T cell associated with multiple sclerosis, an epitope from type-II collagen recognized by a T cell associated with rheumatoid arthritis, an epitope of a red blood cell surface protein recognized by a T cell associated with systemic lupus erythematosus, an epitope from a cell surface antigen of a β cell of the Islets of Langerhans recognized by a T cell associated with insulin-dependent diabetes mellitus, or an epitope from the α subunit of the acetylcholine receptor recognized by a T cell associated with myasthenia gravis. As used herein, a "T cell associated with" a disease is a T cell isolable from a subject having the disease. As used herein, a T cell "recognizes" an epitope if the T cell binds to an MHC Class II molecule having the peptide epitope bound to its antigen binding site. The binding of a T cell to an MHC class II molecule bearing the epitope can be detected by the release of IL-2 or interferon by the T cell. The ELISPOT assay typically is used for such determinations. See, e.g., C. Czerkinsky et al., "Reverse ELISPOT assay for clonal analysis of cytokine production," *J. Immunol. Meth.,* (1988) 110: 29–36.

More particularly, the MBP epitope, DENPVVHFFK NIVTPRTPP (SEQ ID NO:2), when modified according to this invention, has greater binding affinity for HLA-DR2 molecules.

Human collagen type II contains motifs having the sequence GPPG (SEQ ID NO:16) or $GX_1GPPGX_2G$ (SEQ ID NO:17), wherein $X_1$, and $X_2$ are amino acids. Peptides containing this sequence are capable of binding to a HLA-DR4. Complexes between peptide epitopes having this motif and HLA-DR4 are useful in treating rheumatoid arthritis.

Peptide epitopes of such antigens can be identified by several means. In one method, the antigen can be cleaved into smaller peptides by proteolysis. The peptides can then be tested for their ability to bind MHC molecules. Alternatively, when the amino acid sequence of the protein is known, series of peptides can be prepared that have overlapping sequences corresponding to amino acid sequences within the protein antigen. Antigenic peptides also can be identified by screening synthetic peptide libraries for those peptides capable of binding to MHC molecules. Methods for identifying antigenic peptides are described further in U.S. Pat. No. 5,468,481.

Peptides preferably are prepared by routine chemical means for peptide synthesis. In the alternative, they can be made recombinantly using isolated or synthetic DNA sequences. However, this is not the most efficient approach for peptides of this length.

The ability of peptides to bind MHC Class II molecules is readily determined. Purified MHC Class II proteins are incorporated into phospholipid vesicles by detergent dialysis. The resultant vesicles are then allowed to fuse to clean glass cover slips to produce on each a planar lipid bilayer containing MHC molecules (Brian and McConnell, *Proc. Natl. Acad. Sci. USA* (1984) 81: 6159). The peptides to be tested are detectably labeled and then incubated on the plates with purified MHC proteins which have been formulated into lipid membrane bilayers. Peptides that bind to the MHC molecules are identified by detecting label bound to the plate.

B. Methods of Increasing the Binding Affinity Antigenic Peptides to MHC Molecules The affinity of a peptide epitope for an MHC molecule is increased by coupling a hydrophobic amino acid or a peptide containing a hydrophobic amino acid (together, the "hydrophobic moiety") to the N-terminus of the peptide ("Z"), typically through a peptide bond. The hydrophobic amino acid preferably is tyrosine, but also can be phenylalanine, tryptophan, or histidine.

Preferably, the hydrophobic moiety is a hydrophobic amino acid attached to the N-terminus of the peptide epitope. However, the hydrophobic moiety also can be a peptide moiety of several amino acids that contains a hydrophobic amino acid. In this case it is preferable for the hydrophobic amino acid to be the N-terminal amino acid of the modified antigenic peptide. While not wishing to be limited by theory, it is believed that the attachment of a hydrophobic moiety to the peptide epitope increases its binding affinity by acting as an anchor within the MHC antigen binding pocket. Accordingly, the hydrophobic moiety preferably is attached to the peptide epitope at a location within no more than about ten amino acids from the agretope of the peptide epitope. The agretope is that portion of the peptide epitope that is recognized by the MHC molecule.

Addition of an N-terminal hydrophobic amino acid increases the binding affinity of peptide epitopes for MHC Class II molecules including, in the case of human MHC Class II molecules, HLA-DR, HLA-HLA-DQ or HLA-DP. In particular, the modification of peptide epitopes for HLA-DR2 and HLA-DR4 molecules by the methods of this invention increases their binding affinity, especially peptide epitopes of MBP.

Modified antigenic peptides preferably are prepared by routine chemical synthesis. Also, they can be made by recombinant production.

II. MHC-Modified Peptide Complexes

Modified antigenic peptides are bound to isolated MHC Class II molecules to create MHC-modified peptide complexes that are useful in inactivating T cells that recognize an epitope of the antigenic peptide.

MHC-modified peptide complexes consist essentially of at least two components: an MHC Class II component and a modified antigenic peptide. The MHC Class II component has an antigen binding site to which the peptide is bound, and is capable of presenting the modified antigenic peptide to a CD4+ T cell. The term "consisting essentially of" is used herein to mean that the complexes of the invention are at least partially purified and are not complexes in their natural state, e.g., complexes associated with naturally occurring cells where they exist as macromolecular entities on the cell surface, or complexes in a crude cell homogenate. The association between the modified antigenic peptide and the antigen binding sites of the MHC molecule or subunit can be by covalent or non-covalent bonding.

In one aspect, the complex of this invention is capable of inactivating a target T cell. As used herein, "inactivation" refers to induction of anergy or apoptosis. "Anergy" refers to a state in which a target T cell is non-responsive to an antigen presenting cell, e.g., fails to release a lymphokine, or fails to respond to an infected cell by the release of cytotoxic chemicals, in response to an antigen that otherwise activates these events. "Apoptosis" refers to the death of a cell characterized by fragmentation of nuclear RNA.

In other embodiments the complexes may also contain an effector component which is generally a toxin or a label. The effector portion may be conjugated to either the HLA-DR4 molecule or subunit, or to the antigenic peptide. Each of the components of the system is described separately below; followed by a description of the methods by which these complexes can be prepared, evaluated and employed.

The production and isolation of MHC-peptide complexes are also described in, for example, U.S, Pat. No. 5,194,425, 5,130,297, 5,260,422 and 5,468,481.

A. The MHC Class II Component

The amino acid sequence of each of a number of Class II proteins are known, and the genes or cDNAs have been cloned. Thus, these nucleic acids can be used to express the MHC polypeptides in a prokaryotic host cell according to the invention, as described herein. The amino acid sequence of HLA-DR4Dw4 is presented in FIG. 7.

If a desired MHC gene or cDNA is not available, cloning methods known to those skilled in the art may be used to isolate the genes. One such method that can be used is to purify the desired MHC polypeptide, obtain a partial amino acid sequence, synthesize a nucleotide probe based on the amino acid sequence, and use the probe to identify clones that harbor the desired gene from a cDNA or genomic library.

MHC polypeptides can be obtained by isolation from lymphocytes and screened for the ability to bind the desired peptide antigen. The lymphocytes are from the species of individual which will be treated with the complexes. For example, they may be isolated from human B cells from an individual suffering from the targeted autoimmune disease. The B cells can first be immortalized by transformation with a replication deficient Epstein-Barr virus, utilizing techniques known in the art.

MHC polypeptides have been isolated from a multiplicity of cells using a variety of techniques including solubilization by treatment with papain, by treatment with 3M KCl, and by treatment with detergent. In a preferred method detergent extraction of Class II protein from lymphocytes followed by affinity purification is used. Detergent can then be removed by selected methods such as dialysis. Purification methods for MHC polypeptides are also discussed in the preceding section.

After isolation of the protein, a partial amino acid sequence is determined and degenerate oligonucleotide probes, designed to hybridize to the desired gene, are synthesized. Amino acid sequencing is performed and oligonucleotide probes are synthesized according to standard techniques as described, for instance, in Sambrook et al., (1989) *Molecular Cloning: A Laboratory Manual* (2nd ed.), Vols. 1–3, Cold Spring Harbor Laboratory.

Genomic or cDNA libraries are prepared according to standard techniques as described, for instance, in Sambrook et al., supra. To construct genomic libraries, large segments of genomic DNA are generated by random fragmentation and are ligated with vector DNA to form concatemers that can be packaged into the appropriate vector. Two kinds of vectors are commonly used for this purpose, bacteriophage lambda vectors and cosmids.

To prepare cDNA, mRNA from the organism of interest is first isolated. Eukaryotic mRNA has at its 3' end a string of adenine nucleotide residues known as the poly-A tail. Short chains of oligo d-T nucleotides are then hybridized with the poly-A tails serving as a primer for the enzyme reverse transcriptase. This enzyme uses RNA as a template to synthesize a complementary DNA (cDNA) strand. A second DNA strand is then synthesized using the first cDNA strand as a template. Linkers are added to the double-stranded cDNA for insertion into a plasmid or λ phage vector for propagation in *E. coli*.

Identification of clones in either genomic or cDNA libraries harboring the desired nucleic acid segments is performed by either nucleic acid hybridization, or immunological detection of the encoded protein if an expression vector is used. The bacterial colonies are then replica plated on solid support, such as nitrocellulose filters. The cells are lysed and probed with either oligonucleotide probes described above or with antibodies to the desired protein.

Other methods well known to those skilled in the art can also be used to identify desired genes. For example, amplification techniques, such as the polymerase chain reaction (PCR) can be used to amplify the desired nucleotide sequence. U.S. Pat. Nos. 4,683,195 and 4,683,202 describe this method. Sequences amplified by PCR can be purified from agarose gels and cloned into an appropriate vector according to standard techniques.

1. Prokaryotic Expression of MHC Polypeptides

Prokaryotes that are useful as host cells, according to the present invention, most frequently are represented by various strains of *E. coli*. However, other microbial strains can also be used, such as bacilli, for example *Bacillus subtilis*, various species of Pseudomonas, or other bacterial strains.

According to the invention, the MHC polypeptides are expressed from cloned nucleotide sequences that encode the MHC polypeptides by operably linking the truncated or full-length nucleic acids to signals that direct gene expression in prokaryotes. A nucleic acid is "operably linked" when it is placed into a functional relationship with another nucleic acid sequence. For instance, a promoter or enhancer is operably linked to a coding sequence if it affects the transcription of the sequence. Generally, operably linked means that the nucleic acid sequences being linked are contiguous and, where necessary to join two protein coding regions, contiguous and in reading frame.

The genes encoding the MHC molecules may be inserted into an "expression vector", "cloning vector", or "vector," terms which are used interchangeably herein and usually refer to plasmids or other nucleic acid molecules that are able to replicate in a chosen host cell. Expression vectors may replicate autonomously, or they can replicate by being inserted into the genome of the host cell, by methods well known in the art. Vectors that replicate autonomously will have an origin of replication or autonomous replicating sequence (ARS) that is functional in the chosen host cell(s).

Plasmid vectors that contain replication sites and control sequences derived from a species compatible with the chosen host are used. For example, *E. coli* is typically transformed using derivatives of pBR322, a plasmid derived from an *E. coli* species by Bolivar et al., *Gene* (1977) 2: 95. Often, it is desirable for a vector to be usable in more than one host cell, e.g., in *E. coli* for cloning and construction, and in a Bacillus cell for expression.

The expression vectors typically contain a transcription unit or expression cassette that contains all the elements required for the expression of the DNA encoding the MHC molecule in the host cells. A typical expression cassette contains a promoter operably linked to the DNA sequence encoding a MHC polypeptide and a ribosome binding site. The promoter is preferably positioned about the same distance from the heterologous transcription start site as it is from the transcription start site in its natural setting. As is known in the art, however, some variation in this distance can be accommodated without loss of promoter function. In addition to a promoter sequence, the expression cassette can also contain a transcription termination region downstream of the structural gene to provide for efficient termination. The termination region may be obtained from the same gene as the promoter sequence or may be obtained from a different gene.

Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056) and the tryptophan (trp) promoter system (Goeddel et al., *Nucleic Acids Res.* (1980) 8: 4057) and the lambda-derived $P_L$ promoter and N-gene ribosome binding site (Shimatake et al., *Nature* (1981) 292: 128). Any available promoter system that functions in prokaryotes can be used.

Either constitutive or regulated promoters can be used in the present invention. Regulated promoters can be advantageous because the host cells can be grown to high densities before expression of the MHC polypeptides is induced. High level expression of heterologous proteins slows cell growth in some situations. Regulated promoters especially suitable for use in *E. coli* include the bacteriophage lambda $P_L$ promoter, the hybrid trp-lac promoter (Amann et al., *Gene* (1983) 25: 167; de Boer et al., *Proc. Natl. Acad. Sci. USA* (1983) 80: 21, and the bacteriophage T7 promoter (Studier et al., *J. Mol. Biol.* (1986); Tabor et al., (1985). These promoters and their use are discussed in Sambrook et al., supra.

For expression of MHC polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in Bacillus in addition to *E. coli*.

A ribosome binding site (RBS) is also necessary for expression of MHC polypeptides in prokaryotes. An RBS in *E. coli*, for example, consists of a nucleotide sequence 3–9 nucleotides in length located 3–11 nucleotides upstream of the initiation codon (Shine and Dalgarno, *Nature* (1975) 254: 34; Steitz, *In Biological regulation and development: Gene expression* (ed. R.F. Goldberger), vol. 1, p. 349, 1979, Plenum Publishing, NY).

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297–16302.

The MHC polypeptides can be expressed intracellularly, or can be secreted from the cell. Intracellular expression often results in high yields. However, some of the protein may be in the form of insoluble inclusion bodies. Although intracellularly produced MHC polypeptides of the present invention are active upon being harvested following cell lysis, the amount of soluble, active MHC polypeptide may be increased by performing refolding procedures (see, e.g., Sambrook et al., supra.; Marston et al., *Bio/Technology* (1984) 2: 800; Schoner et al., *Bio/Technology* (1985) 3: 151). More than one MHC polypeptide may be expressed in a single prokaryotic cell by placing multiple transcriptional cassettes in a single expression vector, or by utilizing different selectable markers for each of the expression vectors which are employed in the cloning strategy.

A second approach for expressing the MHC polypeptides of the invention is to cause the polypeptides to be secreted from the cell, either into the periplasm or into the extracellular medium. The DNA sequence encoding the MHC polypeptide is linked to a cleavable signal peptide sequence. The signal sequence directs translocation of the MHC polypeptide through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). Once again, multiple polypeptides can be expressed in a single cell for periplasmic association.

The MHC polypeptides of the invention can also be produced as fusion proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-MHC amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

A preferred system for obtaining recombinant proteins from *E. coli* which maintains the integrity of their N-termini has been described by Miller et al. *Biotechnology* 7: 698–704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

The vectors containing the nucleic acids that code for the MHC polypeptide are transformed into prokaryotic host cells for expression. "Transformation" refers to the introduction of vectors containing the nucleic acids of interest directly into host cells by well known methods. The particular procedure used to introduce the genetic material into the host cell for expression of the MHC polypeptide is not particularly critical. Any of the well known procedures for introducing foreign nucleotide sequences into host cells may be used. It is only necessary that the particular procedure utilized be capable of successfully introducing at least one gene into the host cell which is capable of expressing the gene.

Transformation methods, which vary depending on the type of host cell, include electroporation; transfection employing calcium chloride, rubidium chloride calcium phosphate, or other substances; microprojectile bombardment; infection (where the vector is an infectious agent); and other methods. See, generally, Sambrook et al., (1989) supra, and *Current Protocols in Molecular Biology*, supra. Reference to cells into which the nucleic acids described above have been introduced is meant to also include the progeny of such cells. Transformed prokaryotic cells that contain expression vectors for expressing MHC polypeptides are also included in the invention.

After standard transfection or transformation methods are used to produce prokaryotic cell lines that express large quantities of the MHC polypeptide, the polypeptide is then purified using standard techniques. See, e.g., Colley et al. (1989) *J. Biol. Chem.* 64: 17619–17622; and *Methods in Enzymology,* "Guide to Protein Purification", M. Deutscher, ed. Vol. 182 (1990). The recombinant cells are grown and the MHC polypeptide is expressed. The purification protocol will depend upon whether the MHC polypeptide is expressed intracellularly, into the periplasm, or secreted from the cell. For intracellular expression, the cells are harvested, lysed, and the MHC polypeptide is recovered from the cell lysate (Sambrook et al., supra.). Periplasmic MHC polypeptide is released from the periplasm by standard techniques (Sambrook et al., supra.). If the MHC polypeptide is secreted from the cells, the culture medium is harvested for purification of the secreted protein. The medium is typically clarified by centrifugation or filtration to remove cells and cell debris.

The MHC polypeptides can be concentrated by adsorption to any suitable resin such as, for example, CDP-Sepharose, Asialoprothrombin-Sepharose 4B, or Q Sepharose, or by use of ammonium sulfate fractionation, polyethylene glycol precipitation, or by ultrafiltration. Other means known in the art may be equally suitable.

Further purification of the MHC polypeptides can be accomplished by standard techniques, for example, affinity chromatography, ion exchange chromatography, sizing chromatography, or other protein purification techniques used to obtain homogeneity. The purified proteins are then used to produce pharmaceutical compositions, as described below.

2. Modified MHC Polypeptides

The nucleotide sequences used to transfect the host cells can be modified according to standard techniques to yield MHC polypeptides with a variety of desired properties. The MHC polypeptides of the present invention can be readily designed and manufactured utilizing various recombinant DNA techniques. Many techniques are well known to those skilled in the art, and are provided in the cited references. For example, the MHC polypeptides can vary from the naturally-occurring sequence at the primary structure level by amino acid insertions, substitutions, deletions, and the like. Protein fusions may also be utilized that may confer new activities or combinations of activities on the MHC polypeptide. These modifications can be used in a number of combinations to produce the final modified MHC polypeptide chain.

The amino acid sequence variants can be prepared with various objectives in mind, including facilitating purification and preparation of the recombinant polypeptide. The modified polypeptides are also useful for modifying therapeutic half life, improving therapeutic efficacy, and lessening the severity or occurrence of side effects during therapeutic use. The amino acid sequence variants are usually predetermined variants not found in nature but exhibit the same peptide-binding and T-cell binding activity as native-sequence MHC. For instance, polypeptide fragments comprising only a portion (usually at least about 60–80%, typically 90–95%) of the primary structure may be produced. In certain preferred embodiments, the MHC polypeptides consist essentially of either the $\alpha_1$ or $\beta_1$ domain from the full-length polypeptide. Such fragments typically comprise between about 50 and about 100 amino acids, preferably between about 60 and about 90, more preferably between about 70 and about 80. Alternatively, synthetic methods may be used to prepare polypeptides. See, e.g., Merrifield (1986) *Science* 232: 341–347; Atherton et al., *Solid Phase Peptide Synthesis: A Practical Approach,* IRL Press, Oxford).

In general, modifications of the sequences encoding the MHC polypeptides is readily accomplished by a variety of well-known techniques, such as site-directed mutagenesis (see, Gillman and Smith (1979) *Gene* 8: 81–97, and Roberts, S. et al. (1987) *Nature* 328: 731–734). Most modifications are evaluated by routine screening in a suitable assay for the desired characteristic. For instance, the effect of various modifications on the ability of the polypeptide to bind peptide or affect T-cell proliferation can be easily determined using the assays described below. Modifications of other properties such as redox or thermal stability, hydrophobicity, susceptibility to proteolysis, or the tendency to aggregate are all assayed according to standard techniques.

For certain applications, the MHC cDNA coding sequences are modified to delete the transmembrane domain and express the resulting soluble MHC polypeptides. Truncation of the MHC cDNA may be performed, for example, by oligonucleotide-directed deletion mutagenesis or polymerase chain reaction. Oligonucleotide-directed in vitro mutagenesis is described, for example, by Kunkel et al. (1987) *Meth. Enzymol.* 154: 367–382. See also, *Current Protocols in Molecular Biology,* Ausubel et al., eds., Greene Publishing and Wiley-Interscience, New York (1987 and periodic supplements).

3. Pharmaceutical Use of MHC Polypeptides

The unglycosylated, prokaryotically-expressed MHC polypeptides of the invention can be used to form complexes with a peptide that represents an antigen associated with, for example, autoimmunity, allograft rejection or allergic responses. The components of the complex are chosen to have a desired effect on the immune system. An effective portion of an MHC polypeptide is one that comprises the antigen binding sites and sequences necessary for recognition of the MHC-peptide complex by the appropriate T cell receptor. The MHC component can be either a Class I or a Class II molecule. The association between the peptide antigen and the antigen binding sites of the MHC protein can be by covalent or by noncovalent binding.

B. The Effector Component

In one embodiment, the complexes of the invention are designed to destroy the immune response to the peptide in question. In this instance, the effector portion of the molecule will be, for example, a toxin, a chemotherapeutic agent, an antibody to a cytotoxic T-cell surface molecule, a lipase, or a radioisotope emitting "hard," e.g., β, radiation. For example, a number of protein toxins are well known in the art including ricin, diphtheria, gelonin, Pseudomonas toxin, and abrin. Chemotherapeutic agents include, for example, doxorubicin, daunorubicin, methotrexate, cytotoxin, and anti-sense RNA. Antibiotics can also be used. In addition, radioisotopes such as yttrium-90, phosphorus-32, lead-212, iodine-131, or palladium-109 can be used. The emitted radiation destroys the target T-cells. The toxin also can be adraimycin or mycophenolate.

In some cases the toxin or other effector component is entrapped in a delivery system such as a liposome or dextran carrier; in these cases, either the active component or the carrier may be bound in the complex.

The effector component can also be a labelling moiety. Labeled complexes of the present invention can be used in a variety of in vivo or in vitro applications. For any of these purposes, the complexes may be directly labeled. A wide variety of labels may be employed, such as radionuclides (e.g., gamma-emitting radioisotopes such as technetium-99or indium-111), fluorescers (e.g., fluorescein), enzymes, enzyme substrates, enzyme cofactors, enzyme inhibitors, chemiluminescent compounds, bioluminescent compounds, etc. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications, T cell typing, isolating or labeling specific cells, and the like. For instance, the complexes of the present invention can be used to assay for potential inhibitors of MHC Class II cell interactions. Potential inhibitors can be assayed for the ability to inhibit binding of complexes of the present invention to T cells in the microphysiometer apparatus described above.

For in vivo diagnostic imaging, radioisotopes are typically used in accordance with well known techniques. The radioisotopes may be bound to the protein either directly or indirectly using intermediate functional groups which were well known to those skilled in the art at the time the parent application was filed. For instance, chelating agents such as diethylenetriaminepentacetic acid (DTPA) and ethylenediaminetetraacetic acid (EDTA) and similar molecules have been used to bind proteins to metallic ion radioisotopes. C. F. Meares and D. A. Goodwin, "Linking radiometals to proteins with bifunctional chelating agents," *J. Protein Chem.* 3: 215–228 (1983).

The complexes can also be labeled with a paramagnetic isotope for purposes of in vivo diagnosis, as in magnetic resonance imaging (MRI) or electron spin resonance (ESR), both of which were well known at the time the parent application was filed. For instance, these and related techniques have been used in the diagnosis of rheumatic diseases (see, Namey, in *Textbook of Rheumatology,* Kelley et al (eds.) Saunders, Philadelphia, 1985). In general, any conventional method for visualizing diagnostic imaging can be used. Usually gamma- and positron-emitting radioisotopes are used for camera imaging and paramagnetic isotopes are used for MRI. Thus, the complexes of the present invention can be used to monitor the course of amelioration of an autoimmune response in an individual. By measuring the increase or decrease in the number of targeted T cells, it is possible to determine whether a particular therapeutic regimen aimed at ameliorating the autoimmune disease is effective.

The effector component can be attached to the MHC Class II component or, if its nature is suitable, to the peptide portion. For example, iodine-131 or other radioactive label can often be included in the peptide determinant sequence. Methods for attaching the effector component to the complex are described in detail below.

C. Formation of the Complex

The elements of the complex can be associated by standard means known in the art. The antigenic peptides can be associated noncovalently with the antigen binding sites of the MHC Class II component by, for example, mixing the two components. They can also be covalently bound using standard procedures by, for example, photo affinity labelling, (see e.g., Hall et al., *Biochemistry* 24: 5702–5711 (1985). This method has previously been shown to be effective in covalently binding antigen in peptides to antigen-binding pockets. See, e.g., Leuscher et al., *J. Biol. Chem.,* 265: 11177–11184 (1990) and Wraith et al., *Cell,* 59: 247–255 (1989). Other modes of linkage are obvious to those of skill in the art, and could include, for example, attachment via carbohydrate groups on the glycoproteins, including, e.g., the carbohydrate moieties of the α- and/or β-chains.

Protein effector components can be conjugated to the MHC Class II component or peptide by standard dehydration reactions using carbodiimides. Heterobifunctional linkers such as SPDP, glutaraldehyde and the like can also be used.

The sequence of preparing the complex depends on the components in each instance. For example, in a particular protocol, the peptide portion and MHC Class II component are noncovalently associated by contacting the peptide with the MHC Class II component, e.g., by mixing. The effector is then covalently linked, if desired using commercially available linkers, such as SPDP (Pierce Chemicals) to the MHC Class II molecule. Alternatively, the effector and MHC Class II component may be first conjugated using a dehydration reaction and the conjugate complexed with the peptide component.

If the effector is itself a protein, the entire complex may be made directly from the appropriate encoding DNA using recombinant methods. An oligonucleotide which encodes the peptide is synthesized using the known codons for the amino acid, preferably those codons which have preferred utilization in the organism which is to be used for expression are utilized in designing the oligonucleotide. Preferred codon utilizations for a variety of organisms and types of cells are known in the art. The sequence may then be incorporated (with or without a sequence encoding a peptide loop region) into a sequence encoding the subunit derived from the MHC antigen, utilizing techniques known in the art. The incorporation site will be such that, when the subunit is expressed and folded, the peptide antigen will be available as an epitope for the target T cells. Methods of replacing sequences within polynucleotides are known in the art, examples of which are described in the section on the construction of plasmids.

Figure 6:
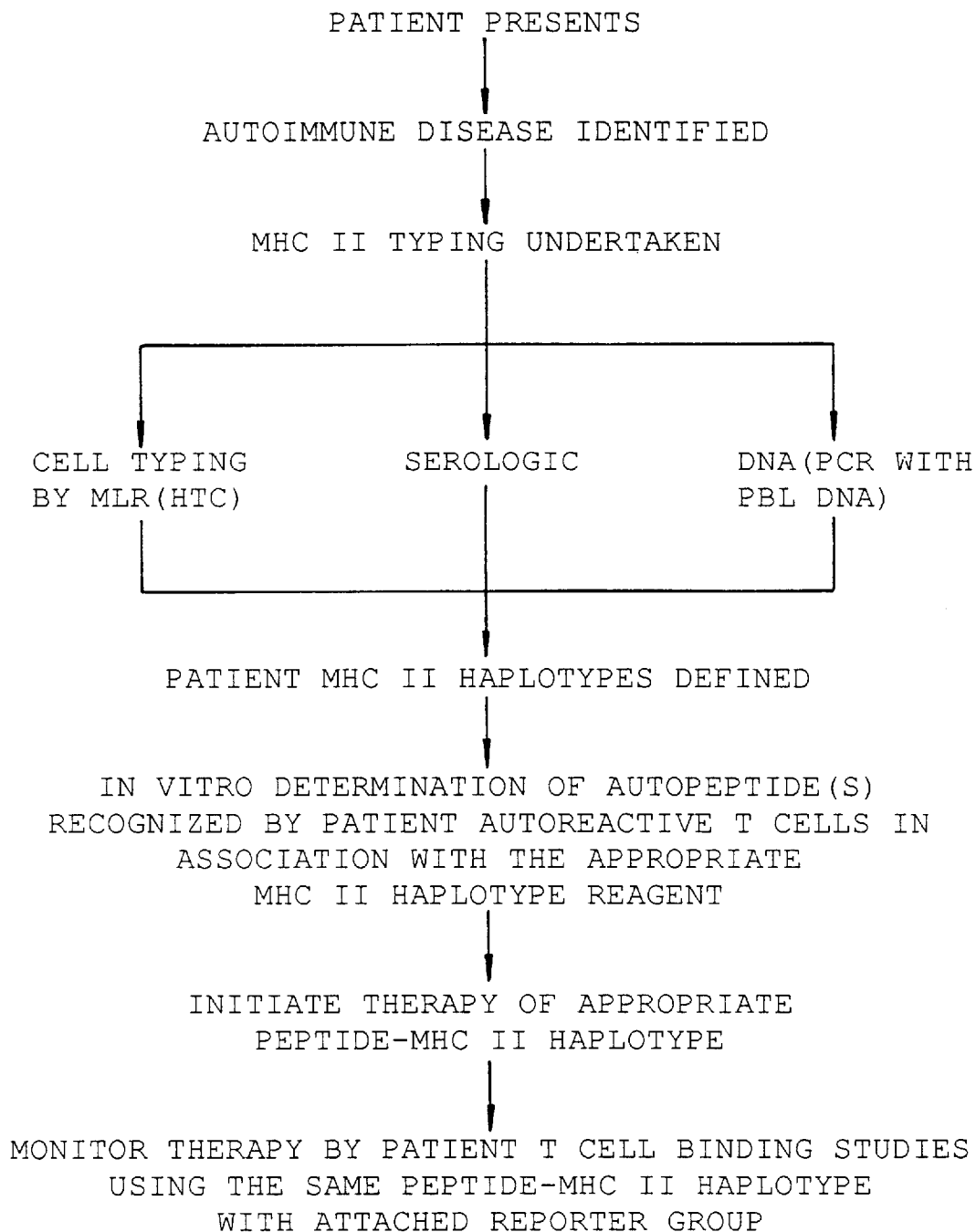
FIG. 6 shows a protocol suitable for the utilization of the complexes of the invention for the diagnosis and/or treatment of an autoimmune disease.

III. Selection of the MHC-Modified Antigenic Peptide Complexes for Therapy and/or Diagnosis A protocol which is suitable for the utilization of the complexes of the invention for the diagnosis and/or treatment of an autoimmune disease is depicted in FIG. 6. Briefly, an individual having (or susceptible to) an autoimmune disease is identified, and the autoimmune dysfunction is identified. Identification may be by symptomology and/or an examination of family histories. The individual's MHC type is determined by one or more of several methods known in the art, including, for example, cell typing by MLR, by serologic assay, and by DNA analysis (including RFLP and PCR techniques). The individuals T cells are examined in vitro, to determine the autopeptide(s) recognized by autoreactive T cells; this is accomplished utilizing labeled complexes of the invention, described, above. After it is determined which complexes target the T cells, the individual is treated with complexes of the invention which are able to suppress the specific autoreactive T cell replication and/or those which kill the autoreactive T cells. Therapy (as determined by the autoreactive T cells remaining) is monitored with T cell binding studies using the labeled complexes of the invention, described, above.

IV. Formulation and Administration

This invention provides pharmaceutical compositions comprising a pharmaceutically acceptable excipient and an MHC Class II-peptide complex of this invention. The complex is included in an amount effective to inactivate a T cell bearing a receptor to which the complex is capable of binding.

If the transmembrane region of the MHC Class II component is included in the complex, the complexes of the invention are conveniently administered after being incorporated or embedded in lipid monolayers or bilayers. Typically liposomes are used for this purpose but any form of artificial lipid membrane, such as planar lipid membranes or the cell membrane of a cell (e.g., a red blood cell) may be used. The complexes are also conveniently incorporated into micelles.

For pharmaceutical compositions which comprise the complexes of the present invention, the dose will vary according to, e.g., the particular complex, the manner of administration, the particular disease being treated and its severity, the overall health and condition of the patient, and the judgment of the prescribing physician. Dosage levels for murine subjects are generally between about 10 µg and about 500 µg. A total dose of between about 50 µg and about 300 µg, is preferred. For instance, in treatments provided over the course of a disease, three 25 µg or 100 µg doses are effective. Total dosages range between about 0.5 and about 25 mg/kg, preferably about 3 to about 15 mg/kg.

The pharmaceutical compositions are intended for parenteral, topical, oral or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

Preferably, the pharmaceutical compositions are administered intravenously. Thus, this invention provides compositions for intravenous administration which comprise a solution of the complex dissolved or suspended in an acceptable carrier, preferably an aqueous carrier. A variety of aqueous carriers may be used, e.g., water, buffered water, 0.4% saline, and the like. For instance, phosphate buffered saline (PBS) is particularly suitable for administration of soluble complexes of the present invention. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the complex can vary widely, i.e., from less than about 0.05%, usually at or at least about 1% to as much as 10 to 30% by weight and will be selected primarily by fluid volumes, viscosities, etc., in accordance with the particular mode of administration selected. Preferred concentrations for intravenous administration are about 0.02% to about 0.1% or 1% or more in PBS.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient.

For aerosol administration, the complexes are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%–20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the complexes can be administered for therapeutic, prophylactic, or diagnostic applications. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient. As discussed above, this will typically be between about 0.5 mg/kg and about 25 mg/kg, preferably about 3 to about 15 mg/kg.

In prophylactic applications, compositions containing the complexes of the invention are administered to a patient susceptible to or otherwise at risk of a particular disease. Such an amount is defined to be a "prophylactically effective dose." In this use, the precise amounts again depend on the patient's state of health and weight. The doses will generally be in the ranges set forth above.

In diagnostic applications, compositions containing the appropriately complexes or a cocktail thereof are administered to a patient suspected of having an autoimmune disease state to determine the presence of autoreactive T cells associated with the disease. Alternatively, the efficacy of a particular treatment can be monitored. An amount sufficient to accomplish this is defined to be a "diagnostically effective dose." In this use, the precise amounts will depend upon the patient's state of health and the like, but generally range from 0.01 to 1000 mg per dose, especially about 10 to about 100 mg per patient.

Kits can also be supplied for therapeutic or diagnostic uses. Thus, the subject composition of the present invention may be provided, usually in a lyophilized form in a container. The complexes, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of complex and usually present in total amount of at least about 0.001% wt. based again on the protein concentration.

Frequently, it will be desirable to include an inert extender or excipient to dilute the active ingredients, where the excipient may be present in from about 1 to 99% wt. of the total composition. Where an antibody capable of binding to the complex is employed in an assay, this will usually be present in a separate vial. The antibody is typically conjugated to a label and formulated according to techniques well known in the art.

Accordingly, this invention provides methods for use with autoimmune diseases. In one aspect, the invention provides methods of inactivating an autoreactive T cell associated with the disease in a subject in need thereof. The method involves administering to the subject an effective amount of a pharmaceutical composition of this invention.

In another aspect, the invention provides methods of destroying an autoreactive T cell associated with a deleterious immune response in a subject in need thereof. The methods involve administering to the subject an effective amount of a pharmaceutical composition of this invention in which the MHC Class II-peptide complex is coupled to a toxin. Upon administration, the toxin is effective to destroy a T cell that recognizes an auto-antigenic peptide of this invention.

In another aspect, the invention provides methods of treating a subject in need of prophylactic or therapeutic treatment of a deleterious immune response. The method involves administering to the subject an effective amount of a pharmaceutical composition of the invention.

As used herein, the term "individual" or "subject" encompasses all mammals and all vertebrates which possess basically equivalent MHC systems, including humans. As used herein, a "patient" is a subject suffering from a disease. As used herein, a "subject in need thereof" is a subject suffering from a deleterious immune response or a subject who is at risk of developing such disease. As used herein, an "effective amount" is an amount effective to produce the intended result of the method, e.g., inactivating a T cell, by inducing anergy or apoptosis, or treatment. As used herein, the term "treatment" refers to both prophylactic and therapeutic treatments that result in prevention of disease, diminished severity of disease, or amelioration of the disease condition.

In another aspect, this invention provides methods useful for determining whether a subject has T cells associated with a deleterious immune response, such as an autoimmune disease. The methods involve contacting a sample from the subject from a tissue containing T cells with a complex of the invention bearing a labelling moiety, and determining whether label becomes attached to a T cell. Attachment indicates that the T cell bears a receptor that recognizes the complex. Such T cells can be T cells associated with the deleterious immune response.

V. Example

Biotinylated peptides with or without tyrosine residues as well as replaced amino acids at the N-terminus were synthesized by solid-phase peptide synthesis. Various peptides and their sequences are as follow:

| SEQ ID NO: | | |
|---|---|---|
| 1 | Bt-MBP(83-102)Y83 | Bt-YDENPVVHFF KNIVTPRTPP-NH$_2$ |
| 2 | Bt-MBP(84-102) | Bt-DENPVVHFFK NIVTPRTPP-NH$_2$ |
| 3 | Bt-MBP(83-102)A83 | Bt-ADENPVVHFF KNIVTPRTPP-NH$_2$ |
| 4 | Bt-MBP(83-102)K83 | Bt-KDENPVVHFF KNIVTPRTPP-NH$_2$ |
| 5 | Bt-MBP(83-102)D83 | Bt-DDENPVVHFF KNIVTPRTPP-NH$_2$ |
| 6 | Bt-MBP(83-102)Q83 | Bt-QDENPVVHFF KNIVTPRTPP-NH$_2$ |
| 7 | Bt-MBP(83-102)F83 | Bt-FDENPVVHFF KNIVTPRTPP-NH$_2$ |
| 8 | Bt-Bt-MBP(124-143) | Bt-GFGYGGRASD YKSAHKGFKG-NH$_2$ |
| 9 | Bt-MBP(143-168) | Bt-FKGVDAQGTL SMFKLGGRD-NH$_2$ |
| 10 | Bt-E.alpha | Bt-ASFEAQGALA NIAVDKA-NH$_2$ |
| 11 | Bt-E.alpha + Y | Bt-YSFEAQGALA NIAVDKA-NH$_2$ |
| 12 | Bt-MSA | Bt-KPKATAEQLK TVMDD-NH$_2$ |
| 13 | Bt-MSA + Y | Bt-YKPKATAEQL KTVMDD-NH$_2$ |
| 14 | Bt-GAD 35 (NH$_2$) | Bt-SRLSKVAPVI KARMMEYGTT-NH$_2$ |
| 15 | Bt-GAD 35 (NH$_2$) + Y | Bt-YSRLSKVAPV IKARMMEYGTT-NH$_2$ |
| 14 | Bt-GAD 35 (OH) | Bt-SRLSKVAPVI KRRMMEYGTT-OH |
| 15 | Bt-GAD 35 (OH) + Y | Bt-YSRLSKVAPV IKARMMEYGTT-OH |

MBP peptides were used for the binding to HLA-DR2 whereas E-alpha, MSA and GAD peptides were used for the binding to IAg7 (murine MHC class II from NOD mice).

In order to compare the binding of various MBP peptides to DR2, purified DR2 at a concentration of 20 $\mu$g/ml was incubated with 50-fold molar excess of Bt-MBP peptides for 72 hours at varying pH, ranging from pH 5–10 binding buffer at 37° C. The resulting complexes were analyzed for amount of bound peptide by antibody capture plate assay using an enzyme conjugated avidin system as described recently (Mukku et al. (1995) "pH dependent binding of high and low affinity myelin basic protein peptides to purified HLA-DR2." *Mol. Immunol.* 32: 555). Monoclonal antibody against HLA-DR2 at a concentration of 20 $\mu$g/ml and BSA-biotin (with 0.014–1.80 pmoles (0.117–15 ng), were coated in 96-well microtiter plates (Nunc poly-Sorb, Baxter) overnight at 4° C. Plates were blocked with 1% fish gelatin. Prepared HLA-DR2-biotin peptide complexes were applied to the wells in duplicates ranging from 12.5 ng–200 ng (0.21–3.32 pmoles) in appropriate dilution buffers and incubated for 2 hours at room temperature. The wells were washed three times with PBS containing 0.01% Tween-20 to remove unbound peptide. Bound biotinylated peptides were detected colorimetrically using alkaline phosphatase conjugated streptavidin and p-nitrophenyl phosphate (disodium) in 0.1M diethnolamine as a substrate. Wells were read at 405 nm in microliter plate reader (Molecular Devices). The percent of DR2 with bound peptide was calculated using standard BSA-biotin (eight biotin molecules per BSA). Purified HLA-DR2 used in this study contains a mixture of DRB5*0101 and DRB1*1501 beta chains.

Figure 2:
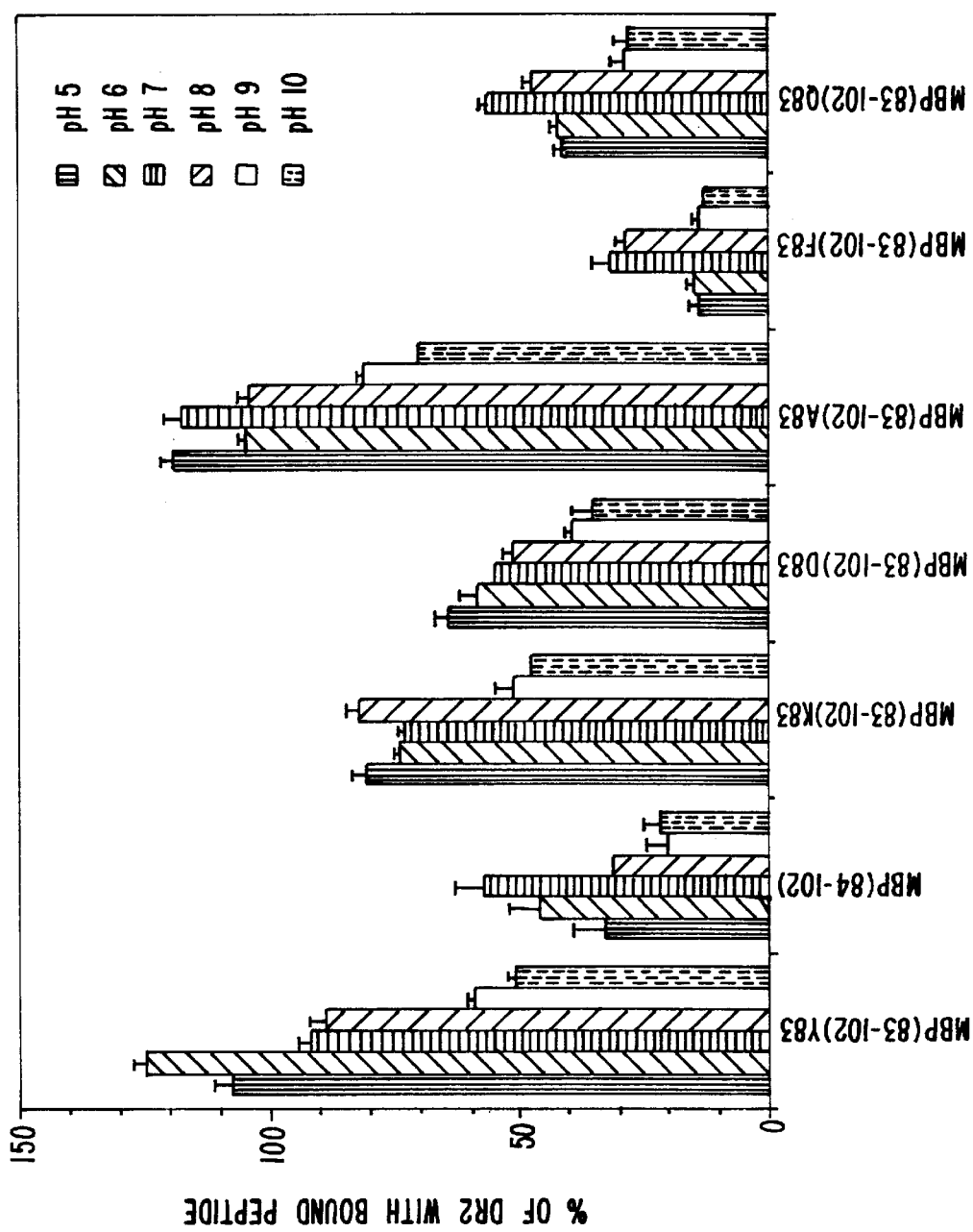
FIG. 2 presents the binding data of various MBP peptides with replaced amino acids.
Figure 3:
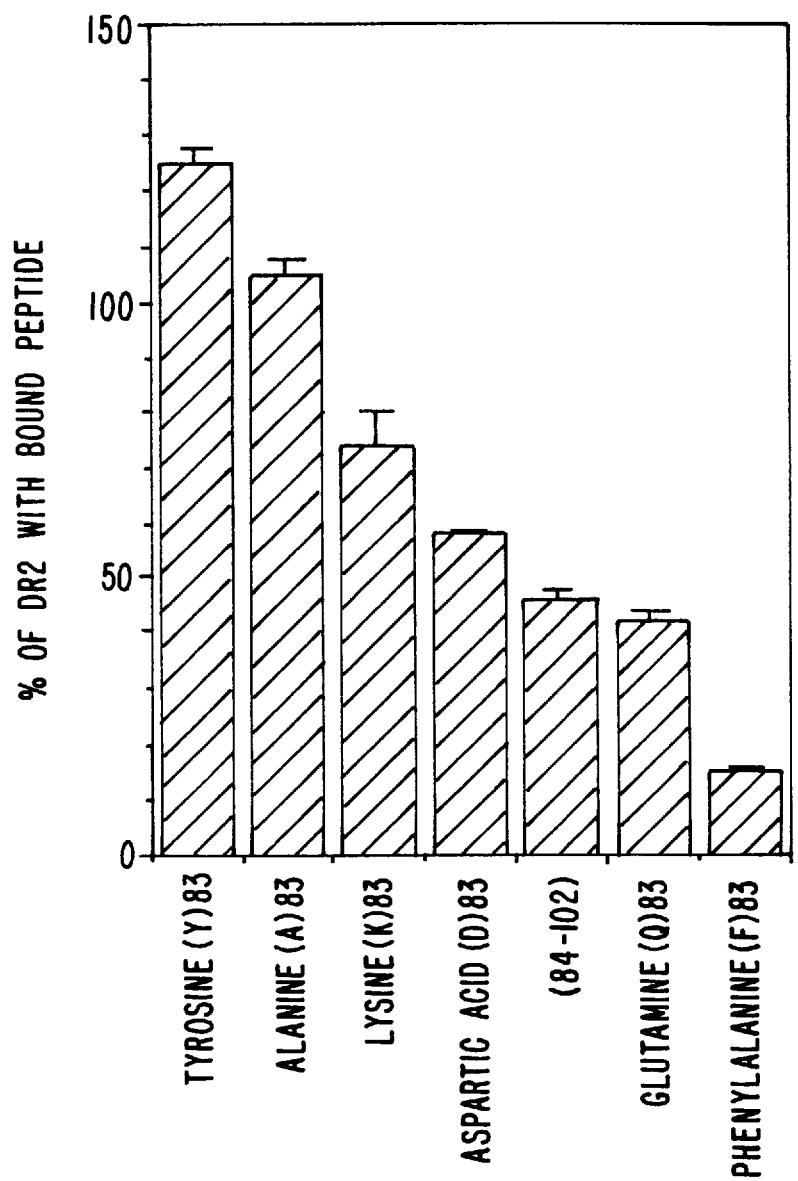
FIG. 3 compares the percent binding of purified DR2 at pH 6.0 with various MPB(83–102) peptides having different amino acids at position 83.

In the first experiment, the binding of MBP(84–102) peptide to purified DR2 was compared with MBP(83–102) Y83 peptide at various pH. As shown in FIG. 1, the binding of tyrosine containing MBP(83–102)Y83 peptide to DR2 was higher at all pH of the binding buffer. Similar experiments were performed where position 83 of the MBP (83–102)Y83 peptide was replaced with various amino acids. The binding data of various MBP peptides with replaced amino acids are presented in FIG. 2. Among all peptides, MBP(83–102)Y83 and MBP(83–102)A83 showed maximum binding at around acidic pH. When compared the binding of various MBP peptides to DR2 at pH 6, the tyrosine containing peptide (MBP(83–102)Y83) showed maximum binding to purified HLA-DR2 (FIG. 3). Other MBP peptides with alanine, lysine, aspartic acid, glutamine and phenylalanine substitution at position 83 occupied 100, 75, 55, 40 and 12% of DR2, respectively. MBP peptide without the tyrosine residue showed 45% occupancy of DR2.

Figure 4:
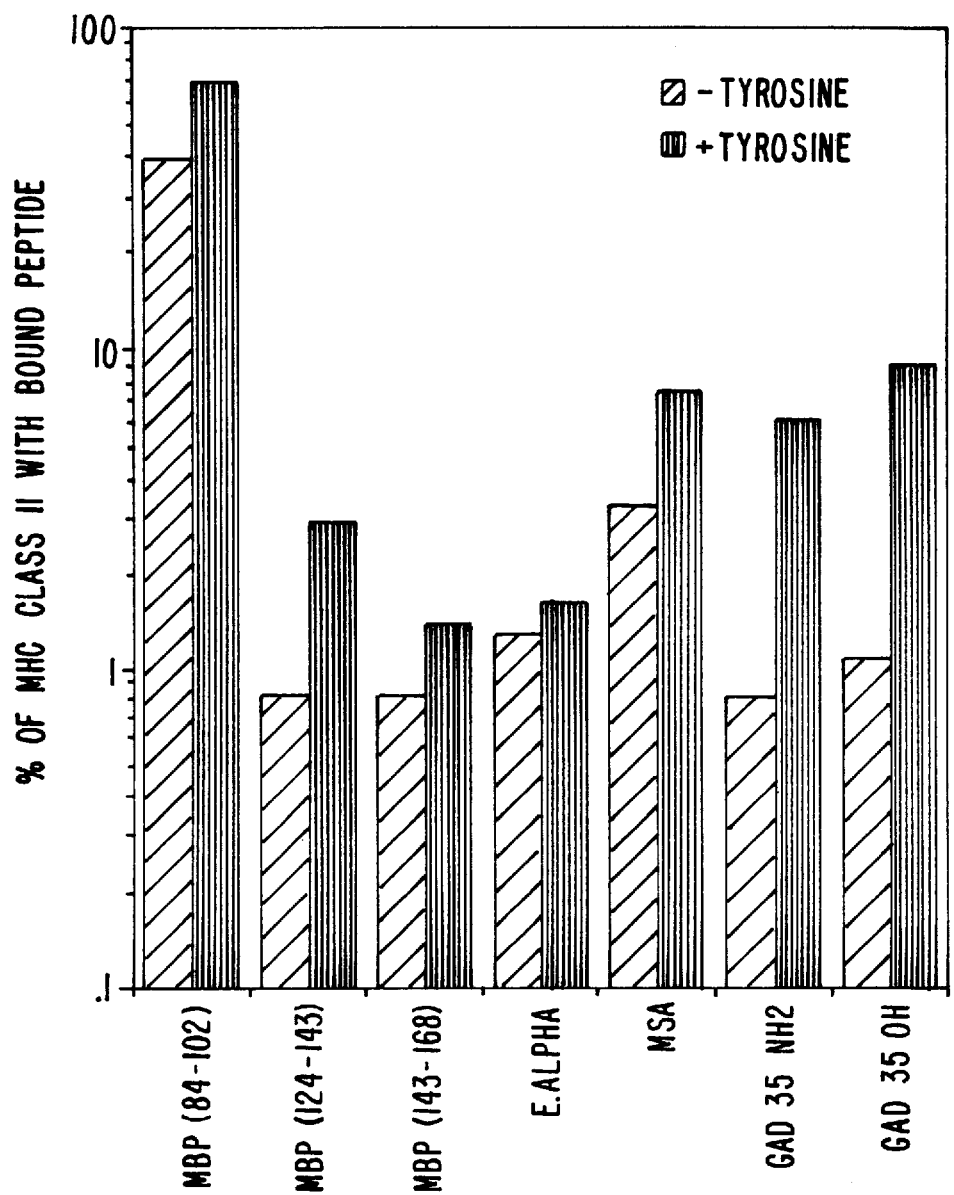
FIG. 4 compares the binding of various peptides with and without an N-terminal tyrosine to HLA-DR2.

To ensure that the observed increase in binding of MBP peptide with tyrosine to HLA-DR2 is not restricted to only this system, various other peptides with and without tyrosine residues were synthesized and tested. In all cases, as shown in FIG. 4, an increase in binding of tyrosine containing peptides were observed as compared to non-tyrosine containing peptides. Although the magnitude of the increased binding varied from peptide to peptide, in most cases the presence of the tyrosine residue at the N-terminus has 100% increased occupancy of class II molecules with respective peptides.

Figure 5:
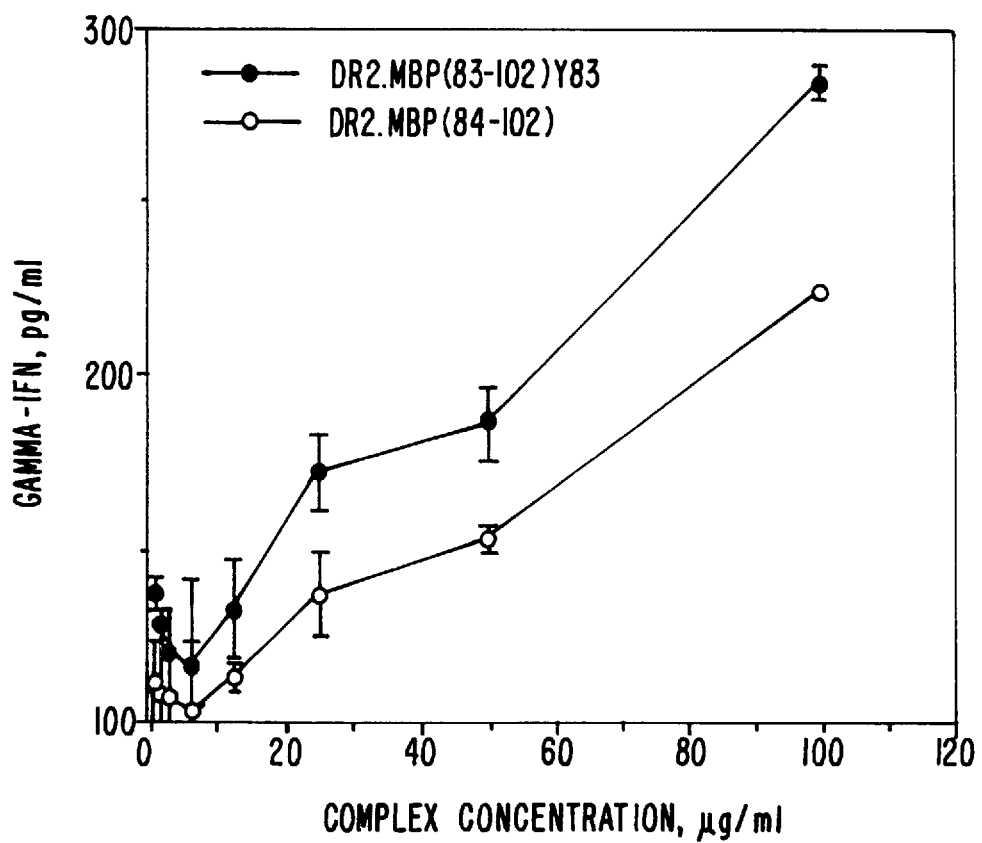
FIG. 5 compares the amount of gamma-IFN released by T cells exposed to complexes of HLA DR2 with MBP (83–102)Y83, and HLA DR2 with MBP(84–102).

Finally, the role of tyrosine residue at position 83 of the MBP peptide was examined in TCR occupancy assay using DR2.MPB(84–102) restricted transformed T cell clone (SS8T). The detail characterization of the SS8T T cell clone is described separately (Weber et al. (1993) "Transformation of human T-cells clones by Herpesvirus saimiri: intact antigen recognition by autonomously growing myelin basic protein-specific T cells." *Proc. Natl. Acad. Sci. USA* 90: 11049). T cells were incubated with equivalent amount of purified complexes containing either MPB(84–102) or MBP (83–102)Y83 peptide, and the increase in gamma-IFN was measured upon TCR engagement. As shown in FIG. 5, the presence of tyrosine residue has increased level of gamma-IFN as compared to non-tyrosine native sequence at all concentrations.

The present invention provides novel modified antigenic peptides having improved binding ability for MHC molecules and methods for their use. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A Major Histocompatibility Complex "MHC" Class II-modified peptide complex capable of binding a T cell receptor comprising:
    an MHC Class II component comprising an antigen binding site; and
    an antigenic peptide of the formula human MBP(83–102) Y83, wherein the antigenic peptide is bound to the antigen binding site.

2. The complex of claim 1 wherein the MHC Class II component is an HLA component.

3. The complex of claim 2 wherein the HLA component is and HLA-DR4 component.

4. The complex of claim 1, wherein the MHC Class II component comprises and intact extracellular domain of an MHC Class II molecule.

5. The complex of claim 1, wherein the MHC Class II component comprises an MHC Class II single chain.

6. The complex of claim 1 further comprising an effector component.

7. The complex of claim 1 that is a fusion protein.

8. The complex of claim 2 wherein the HLA component is an HLA-DR2 component.

9. A pharmaceutical composition comprising a pharmaceutically acceptable excipient and a Major Histocompatibility Complex "MHC" Class II-modified peptide complex capable of binding a T cell receptor, the complex being present in an amount effective to inactivate a T cell bearing the receptor, the complex comprising:
    an MHC Class II component comprising an antigen binding site; and
    an antigenic peptide of the formula human MBP(83–102) Y83, wherein the antigenic peptide is bound to the antigen binding site; the complex being capable of binding a T cell receptor on a T cell.

10. The pharmaceutical composition of claim 9 wherein the MHC Class II component is an HLA component.

11. The pharmaceutical composition of claim 10 wherein the concentration of the complex is between about 0.02% and about 1% by weight.

12. The pharmaceutical composition of claim 10 wherein the HLA component is an HLA-DR2 component.

13. The pharmaceutical composition of claim 10 wherein the HLA component is an HLA-DR4 component.

14. A method for preparing a pharmaceutical composition comprising a pharmaceutically acceptable excipient and a Major Histocompatibility Complex"MHC" Class II-modified peptide complex capable of binding a T cell receptor, the complex being present in an amount effective to inactivate a T cell bearing the receptor, the complex comprising:
    an MHC Class II component comprising an antigen binding site; and
    an antigenic peptide of the formula human MBP(83–102) Y83, wherein the antigenic peptide is bound to the antigen binding site; the complex being capable of binding a T cell receptor on a T cell,
    the method comprising:
    isolating the MHC Class II component from a cell capable of producing the component;
    contacting the MHC Class II component with the peptide such that the peptide is bound to the antigen binding site, thereby forming an MHC Class II-peptide complex;
    removing excess peptide not bound to the antigen binding site; and
    mixing the MHC Class II-modified peptide complex with the pharmaceutically acceptable excipient in a ratio suitable for therapeutic or diagnostic administration of the complex.

15. The method of claim 14 wherein the step of removing excess peptide is carried out by dialysis.

16. The method of claim 14 wherein the MHC Class II component is an HLA component.

17. The method of claim 16 wherein the HLA component is an HLA-DR2 component.

18. The method of claim 16 wherein the HLA component is an HLA-DR4 component.

19. A method of inactivating an autoreactive T cell associated with an autoimmune disease in a subject in need thereof, the method comprising administering to the subject an effective amount of a pharmaceutical composition comprising a pharmaceutically acceptable excipient and a Major Histocompatibility Complex "MHC" Class II-modified peptide complex capable of binding a T cell receptor in an amount effective to inactivate a T cell bearing the receptor, the complex comprising:
    an MHC Class II component comprising an antigen binding site; and
    an antigenic peptide of the formula human MBP(83–102) Y83, the antigenic peptide bound to the antigen binding site; the complex being capable of binding a T cell receptor on a T cell.

20. The method of claim 19 wherein the MHC Class II component is and HLA component.

21. The method of claim 20 wherein the HLA component is and HLA-DR2 component.

22. The method of claim 19 wherein the MHC Class II component comprises an intact extracellular domain of an MHC Class II molecule.

23. The method of claim 19 wherein the complex further comprises an effector component.

24. The method of claim 19 wherein the effective amount is between about 50 µg and about 300 µg of the complex.

25. The method of claim 19 wherein the effective amount is between about 3 mg MHC Class II-modified peptide complex per kg body weight and about 15 mg MHC Class II-modified peptide complex per kg body weight.

26. The method of claim 19 wherein the pharmaceutical composition is administered intravenously.

27. The method of claim 20 wherein the HLA component is an HLA-DR4 component.

28. A method of prophylactic or therapeutic treatment of an autoimmune disease in a subject, the method comprising administering to the subject an effective amount of a pharmaceutical composition comprising a pharmaceutically acceptable excipient and a Major Histocompatibility Complex"MHC" Class II-modified peptide complex capable of binding a T cell receptor, the complex being present in an amount effective to inactivate a T cell bearing the receptor, the complex comprising:

an MHC Class II component comprising an antigen binding site; and an antigenic peptide of the formula human MBP(83–102) Y83, wherein the antigenic peptide is bound to the antigen binding site; the complex being capable of binding a T cell receptor on a T cell.

29. The method of claim 28 wherein the MHC Class II component is an HLA component.

30. The method of claim 29 wherein the HLA component is an HLA-DR2 component.

31. The method of claim 29 wherein the HLA component is an HLA-DR4 component.

32. The method of claim 29 wherein the effective amount is between about 50 μg and about 300 μg of the complex.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:1:

Tyr Asp Glu Asn Pro Val Val His Phe Phe Lys Asn Ile Val Thr Pro
1               5                   10                  15

Arg Thr Pro Pro
            20

( 2 ) INFORMATION FOR SEQ ID NO:2:

( i ) SEQUENCE CHARACTERISTICS:
( A ) LENGTH: 19 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:2:

Asp Glu Asn Pro Val Val His Phe Phe Lys Asn Ile Val Thr Pro Arg
1               5                   10                  15

Thr Pro Pro ( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

```
Ala  Asp  Glu  Asn  Pro  Val  Val  His  Phe  Phe  Lys  Asn  Ile  Val  Thr  Pro
1                   5                        10                       15
Arg  Thr  Pro  Pro
             20
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:4:

```
Lys  Asp  Glu  Asn  Pro  Val  Val  His  Phe  Phe  Lys  Asn  Ile  Val  Thr  Pro
1                   5                        10                       15
Arg  Thr  Pro  Pro
             20
```

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:5:

```
Asp  Asp  Glu  Asn  Pro  Val  Val  His  Phe  Phe  Lys  Asn  Ile  Val  Thr  Pro
1                   5                        10                       15
Arg  Thr  Pro  Pro
             20
```

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:6:

```
Gln  Asp  Glu  Asn  Pro  Val  Val  His  Phe  Phe  Lys  Asn  Ile  Val  Thr  Pro
1                   5                        10                       15
Arg  Thr  Pro  Pro
             20
```

( 2 ) INFORMATION FOR SEQ ID NO:7:

( i ) SEQUENCE CHARACTERISTICS:

( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:7:

Phe Asp Glu Asn Pro Val Val His Phe Phe Lys Asn Ile Val Thr Pro
1               5                   10                  15
Arg Thr Pro Pro
            20

( 2 ) INFORMATION FOR SEQ ID NO:8:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:8:

Gly Phe Gly Tyr Gly Gly Arg Ala Ser Asp Tyr Lys Ser Ala His Lys
1               5                   10                  15
Gly Phe Lys Gly
            20

( 2 ) INFORMATION FOR SEQ ID NO:9:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:9:

Phe Lys Gly Val Asp Ala Gln Gly Thr Leu Ser Lys Ile Phe Lys Leu
1               5                   10                  15
Gly Gly Arg Asp
            20

( 2 ) INFORMATION FOR SEQ ID NO:10:

( i ) SEQUENCE CHARACTERISTICS:
( A ) LENGTH: 17 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:10:

Ala Ser Phe Glu Ala Gln Gly Ala Leu Ala Asn Ile Ala Val Asp Lys
1               5                   10                  15
Ala ( 2 ) INFORMATION FOR SEQ ID NO:11:

( i ) SEQUENCE CHARACTERISTICS:
( A ) LENGTH: 17 amino acids
( B ) TYPE: amino acid
( C ) STRANDEDNESS:
( D ) TOPOLOGY: linear (i i) MOLECULE TYPE: peptide (x i) SEQUENCE DESCRIPTION: SEQ ID NO:11:

Tyr Ser Phe Glu Ala Gln Gly Ala Leu Ala Asn Ile Ala Val Asp Lys
1               5                   10                  15
Ala (2) INFORMATION FOR SEQ ID NO:12:

(i) SEQUENCE CHARACTERISTICS:
    (A) LENGTH: 15 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:12:

Lys Pro Lys Ala Thr Ala Glu Gln Leu Lys Thr Val Met Asp Asp
1               5                   10                  15

(2) INFORMATION FOR SEQ ID NO:13:

(i) SEQUENCE CHARACTERISTICS:
    (A) LENGTH: 16 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:13:

Tyr Lys Pro Lys Ala Thr Ala Glu Gln Leu Lys Thr Val Met Asp Asp
1               5                   10                  15

(2) INFORMATION FOR SEQ ID NO:14:

(i) SEQUENCE CHARACTERISTICS:
    (A) LENGTH: 20 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:14:

Ser Arg Leu Ser Lys Val Ala Pro Val Ile Lys Ala Arg Met Met Glu
1               5                   10                  15
Tyr Gly Thr Thr
                20

(2) INFORMATION FOR SEQ ID NO:15:

(i) SEQUENCE CHARACTERISTICS:
    (A) LENGTH: 21 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:15:

Tyr Ser Arg Leu Ser Lys Val Ala Pro Val Ile Lys Ala Arg Met Met
1               5                   10                  15
Glu Tyr Gly Thr Thr
                20

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:16:

Gly Pro Pro Gly
    1

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Region
        ( B ) LOCATION: one-of(2, 7)
        ( D ) OTHER INFORMATION: /note= "Xaa is any amino acid"

( x i ) SEQUENCE DESCRIPTION: SEQ ID NO:17:

Gly Xaa Gly Pro Pro Gly Xaa Gly
    1                    5

( 2 ) INFORMATION FOR SEQ ID NO:18:

( i ) SEQUENCE CHARACTERISTICS:
        ( A ) LENGTH: 203 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:18:

Gly Asp Thr Arg Pro Arg Phe Leu Glu Gln Val Lys His Glu Cys His
1              5                 10               15

Phe Phe Asn Gly Thr Glu Arg Val Arg Phe Leu Asp Arg Tyr Phe Tyr
            20                25                30

His Gln Glu Glu Tyr Val Arg Phe Asp Ser Asp Val Gly Glu Tyr Arg
        35               40               45

Ala Val Thr Glu Leu Gly Arg Pro Asp Ala Glu Tyr Trp Asn Ser Gln
    50                  55              60

Lys Asp Leu Leu Glu Gln Lys Arg Ala Ala Val Asp Thr Tyr Cys Arg
65                70                75              80

His Asn Tyr Gly Val Gly Glu Ser Phe Thr Val Gln Arg Arg Val Tyr
            85                90                95

Pro Glu Val Thr Val Ala Pro Ser Lys Thr Gln Pro Leu Gln His His
            100              105              110

Asn Leu Leu Val Cys Asn Val Ser Gly Phe Tyr Pro Gly Ser Ile Glu
         115               120              125

Val Arg Trp Phe Arg Asn Gly Gln Glu Thr Lys Ala Gly Val Val Ser
    130                  135              140

Thr Gly Leu Ile Gln Asn Gly Asp Trp Thr Phe Gln Thr Leu Val Met
145               150               155             160

Leu Glu Thr Val Pro Arg Ser Gly Glu Val Tyr Thr Cys Gln Val Glu

-continued

```
                            165                         170                         175
    Leu Ser Val Thr Ser Pro Leu Thr Val Glu Trp Arg Ala Arg Ser Glu
                180                         185                     190
    Ser Ala Gln Ser Lys Met Leu Ser Gly Val Gly
            195                     200
```